United States Patent [19]

Conlon et al.

[11] 4,350,586

[45] Sep. 21, 1982

[54] APPARATUS USEFUL WITH A CHROMATOGRAPHY COLUMN

[75] Inventors: Ralph D. Conlon, Wilton; Stanley F. Miles, New Canaan; Roland C. Paradis, Bridgeport, all of Conn.

[73] Assignee: The Perkin-Elmer Corporation, Norwalk, Conn.

[21] Appl. No.: 305,659

[22] Filed: Sep. 25, 1981

[51] Int. Cl.³ .............................................. G01N 15/08
[52] U.S. Cl. ................................... 210/149; 210/179; 210/198.2; 55/197; 55/208
[58] Field of Search ............... 210/175, 149, 198.2, 210/184, 186; 55/197, 386, 208

[56] References Cited

U.S. PATENT DOCUMENTS

| 3,782,078 | 1/1974 | Jerpe | 210/198.2 |
| 3,926,800 | 12/1975 | Stedhens | 55/197 X |
| 4,088,458 | 5/1978 | Jourdan | 55/197 |

FOREIGN PATENT DOCUMENTS 636078 2/1962 Canada ................................ 55/386

Primary Examiner—John Adee
Attorney, Agent, or Firm—S. A. Giarratana; F. L. Masselle; R. A. Hays

[57] ABSTRACT

An apparatus for controlling the temperature of a chromatography column includes a pair of base members which include means for receiving and substantially uniformly contacting the periphery of a chromatography column. Means for controlling the temperature of the column receiving means is also provided.

13 Claims, 5 Drawing Figures

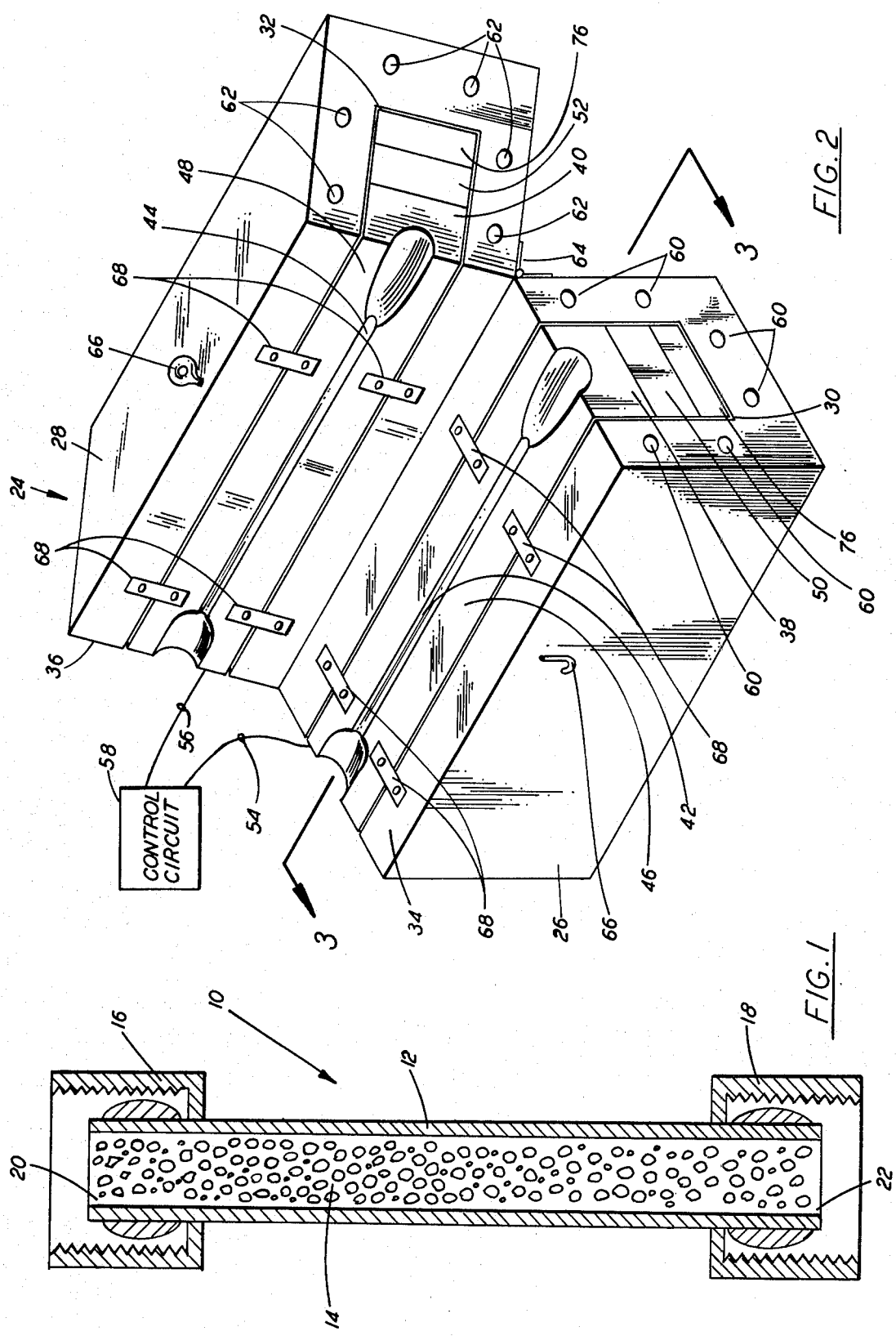

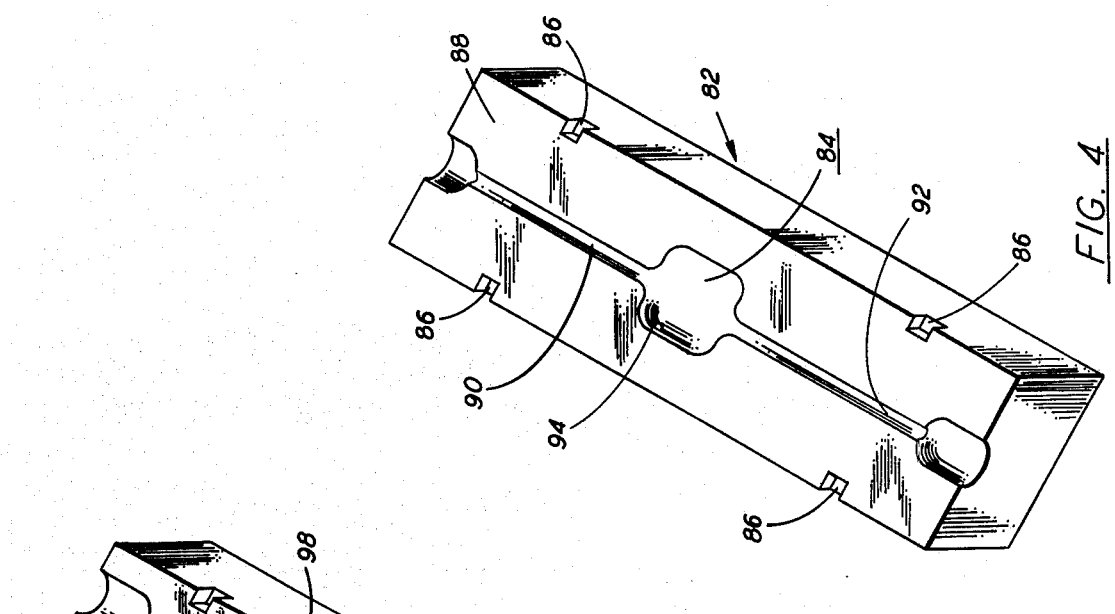
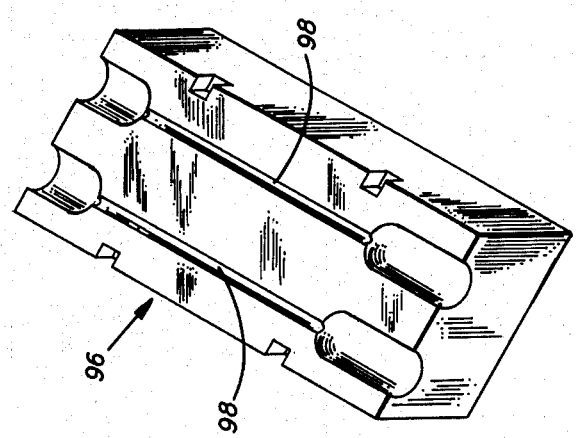
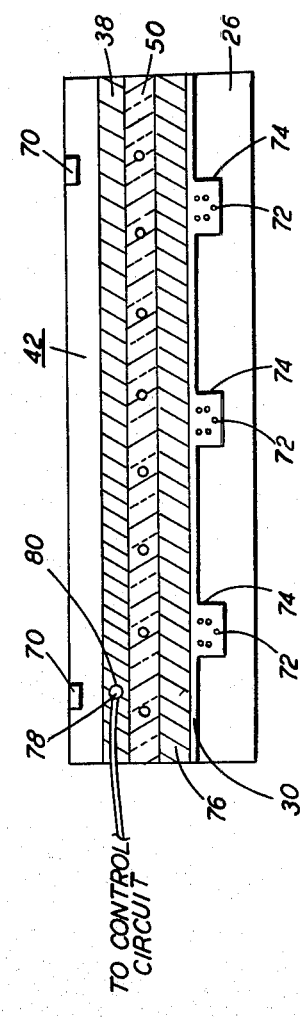

APPARATUS USEFUL WITH A CHROMATOGRAPHY COLUMN

BACKGROUND OF THE INVENTION

The present invention generally relates to an apparatus useful with a chromatography column and, in particular, relates to an apparatus for maintaining a chromatography column at a uniform temperature.

In the general field of chromatography, it is well known that the successful analysis of a sample flowing through a chromatography column is often dependent upon the temperature of the column. The temperature of the column has a direct influence on almost all of the critical parameters of such an analysis. For example, in liquid chromatography; the viscosity of the solvent (and hence its fluidity and therefore its flow rate and back pressure); the retention of the sample by the stationary phase (and hence the clarity of sample component separation); the temperature gradient, if any, along the length of the column, such gradients are set up by what is commonly known as "heat of friction" and can easily be a significant influence, (and hence the reproducibility and uniform reliability of the separation); the temperature gradient, if any, across the cross-section of the column (and hence the uniformity of flow of the fluid front along the column upon which the distinctiveness of separation depends), as well as other critical parameters, are highly dependent upon the temperature of the column. Without a doubt, these are but a few of the factors taken into account during a chromatographic analysis, even when it is performed at, for example, room temperature. The magnitude of these difficulties is compounded when the analysis is performed at reduced or elevated temperatures.

Generally, insofar as liquid chromatography columns are concerned, the above-recited difficulties have been dealt with by use of either one of two means. In one prior art means, the column is located in a heated box, or oven. While this means reduces the effects of the difficulties, severe temperature gradients nonetheless exist and detrimentally influence the analysis. Such gradients exist primarily from the inability of conventional ovens to maintain uniform temperatures therein and thus such ovens require the continuous cycling of the heating element. Further, conventional ovens require the introduction of more heat than necessary to warm the surrounding air which is often cooler than the desired temperature. One major concern in this type of apparatus is the inherent time lag between the introduction of heat and the response of the temperature measuring means, e.g., a thermocouple. Further, because of the poor heat transfer between the oven air and the metal column, the top of the column is cooled rapidly by the influx of room temperature solvent. Consequently, a steep temperature gradient, as much as 15° C., is created. Such a large temperature gradient inevitably reduces the separation efficiency of the column. As a consequence, the column within such an oven is not uniformly heated.

The other commonly used means is a generally heated column holder having a V-groove therein for generally positioning the column. Such an apparatus is unsatisfactory since the holder only contacts the column along two points of the V. Occasionally, a pair of these holders are used and thus the number of contact points becomes doubled. However, since the column is not uniformly contacted or secured, temperature gradients are formed both along the length of the column and across its cross-section.

Hence, it is highly desirable to provide an apparatus which substantially completely eliminates both axial and radial temperature gradients in a column during an analysis. The need is particularly great when an analysis is performed which requires the use of a guard column or a second column in series with a chromatography column.

SUMMARY OF THE INVENTION

From the foregoing it is one object of the present invention to provide an apparatus for maintaining a chromatography column at a uniform temperature.

This object is accomplished, at least in part, by an apparatus including first and second base members each having associated therewith means for receiving a column such that the peripheral surface thereof is substantially completely contacted as well as means for controlling the temperature of the receiving means.

Other objects and advantages will become apparent to those skilled in the art from the following detailed description and accompanying drawing.

BRIEF DESCRIPTION OF THE DRAWING

The drawing, which is not drawn to scale, includes:

FIG. 1, which is a pictorial view of a typical liquid chromatography column;

FIG. 2, which is a pictorial view of one embodiment of an apparatus incorporating the principles of the present invention;

FIG. 3, is a sectional view of the apparatus shown in FIG. 2 taken along the line 3—3 thereof;

FIG. 4, is another embodiment of an insert useful in the apparatus shown in FIG. 2; and FIG. 5, is yet another embodiment of an insert useful in the apparatus shown in FIG. 2.

DETAILED DESCRIPTION OF THE INVENTION

A typical liquid chromatography column, indicated generally at 10 in FIG. 1, includes a cylindrical tube 12 into which stationary phase material 14 is packed. In general, conventional columns are manufactured from stainless steel, glass or the like, vary in length from less than 10 cm. to about 30 cm. and vary in outside diameter from about 0.6 cm. to about 3.5 cm. The selection of stationary phase material and the dimensions of a particular column are dependent upon the sample material, and the constituents thereof to be separated. These choices are so well known in the art that further discussion is not deemed necessary for the purpose of describing the present invention.

As shown in FIG. 1, the column 10 is equipped with threaded connectors, 16 and 18, at the ends, 20 and 22, respectively, thereof. The connectors, 16 or 18, or fittings, are also well known in the art and are usually supplied with the column 10 when it is sold.

An apparatus, generally indicated at 24 in the drawing, and embodying the principles of the present invention, includes a first base member 26 and a second base member 28. In the preferred embodiment, the first and second base members, 26 and 28, respectively, are fabricated from aluminum or some other thermally conductive material. Each base member, 26 and 28, includes a recess, 30 and 32, respectively, in a major surface, 34 and 36, respectively, thereof. The recesses, 30 and 32, in the preferred embodiment, are about 2.5 cm. wide and extend into the respective major surfaces, 34 and 36, about 2 cm. Of course, the dimensions of the recesses, 30 and 32, can be adjusted to accommodate the larger diameter columns.

Each recess, 30 and 32, has at least one means, 38 and 40, respectively, associated therewith for substantially uniformly receiving the column 10. Each means, 38 or 40, is formed from a thermally conductive material, such as aluminum, and includes at least one shaped cavity, 42 or 44, respectively, in one major surface, 46 or 48, thereof. As clearly shown in FIG. 2 of the drawing, the cavities, 42 and 44, in that embodiment are shaped so as to accept about half of the depth of the column 10 in each means, 38 and 40, respectively. Thus, when the base members, 26 and 28, are closed one upon the other, the periphery of the column 10 is substantially completely embraced in the cavities, 42 and 44, associated therewith. Preferably, the means, 38 and 40, are cooperatively sized with the recesses, 30 and 32, so that when the means, 38 and 40, are located therein, they do not protrude beyond the major surfaces, 34 and 36.

Additionally, each column receiving means, 38 and 40, has associated therewith a furnace means, 50 and 52, respectively. In the preferred embodiment each furnace means, 50 and 52, is an encapsulated resistance heater. The furnace means, 50 and 52, include electrical leads, 54 and 56, which are connected to a control circuit 58.

In one particular embodiment, each base member, 26 and 28, also includes means, 60 and 62, respectively, therein for conveying a coolant therethrough. In practice, most liquid chromatography analyses requiring a cooled column are performed above the freezing point of water and thus cold water can usually be used as the coolant liquid.

For reasons more fully discussed below, the first and second base members, 26 and 28, respectively, are affixed to each other by a hinge means 64 whereby when the major surfaces, 34 and 36, respectively, are closed one upon the other, the recesses, 30 and 32, respectively, therein are aligned with each other. The base members, 26 and 28, also include latching means 66 for maintaining the base members, 26 and 28, in a closed position. The latching means 66 can be any such means known in the art, such as a hook-and-eye arrangement.

Preferably, the means, 38 or 40, or inserts, are securely retained in the recesses, 30 and 32, respectively, by a plurality of tabs 68. In the preferred embodiment, the tabs 68 are positioned in aligned slots 70, most clearly shown in FIGS. 4 and 5, in both the base members, 26 and 28 and the means 38 and 40. The slots 70 are cooperatively sized with the tabs 68 so that the tabs 68 are flush with the major surfaces, 34 and 36. The tabs 68 can be secured in place by any means known in the art, such as, for example, screws inserted through openings therein, which openings can be designed to fully accept the head of the screws to avoid any protrusion above the major surfaces 34 and 36. The use of the above-described tabs 68 not only provide a means for aligning the column receiving means, 38 and 40, but also ensure a uniform thermal interface between each means 38 or 40, and its associated base member, 26 or 28, respectively.

In order to ensure substantially uniform contact between the cavities, 56 and 58, and substantially the periphery of the column 10, the means, 38 and 40, are biased away from the recesses 30 and 32. In the preferred embodiment, the biasing is provided by a plurality of coil springs 72 positioned in, and secured to, the bottom of a plurality of openings 74 which extend into the base members 26 and 28 from the recesses 30 and 32. Thus, when the column 10 is inserted into one cavity, for example 42, and the base members, 26 and 28, are closed one upon the other, the aligned cavities, 42 and 44, enclose and securely embrace, due to the bias springs 72, the column 10 about its periphery, whereby a uniform thermal conductivity interface exists between the column 10 and the base members 26 and 28 via the column receiving means 38 and 40. In order to enhance and uniformly bias the means, 38 and 40, a spacer plate 76 is preferably provided between the furnace 50 and 52, and the springs 72.

It will be understood that the temperature of the column 10 can easily be controlled by circuit means well known in the art. Most such circuits include as a control means therefor a temperature sensing element. In order to provide such an input to the circuit means, a thermocouple 78, or the like, can be provided in one of the base members, such as 26, such that it contacts the means 38. One such embodiment is shown in FIG. 3 wherein the thermocouple 78 is located in a contoured aperture 80 and positioned in thermal contact with the means 38.

Referring to FIG. 4, there is shown therein another embodiment of the column receiving means 38, designated in this Figure as 82. Like the aforedescribed means 38, the column receiving means 82 includes a shaped cavity 84 and a plurality of tab receiving slots 86 extending into a major surface 88 thereof.

In this embodiment, the cavity 84 generally includes three distinct portions, 90, 92, and 94. The first portion 90 is dimensioned to accept therein an analytical column, a guard column or a precolumn (not shown in the drawing). The use of guard or precolumns is well known in the chromatography field and, as depicted, such columns usually have the same diameter as the analytical column 10.

The second portion 92 is dimensioned to accept therein an analytical column, like the column 10. The third portion 94 is dimensioned to accept a pair of interconnected fittings which interconnection serially joins a guard column and an analytical column.

In operation, two of these receiving means 82 are utilized, one in each recess 30 and 32 of the base members, 26 and 28, respectively.

Yet another embodiment, further demonstrating the versatility of the present invention, is shown in FIG. 5. Therein a column receiving means 96 includes a pair of shaped cavities 98. The cavities 98, while shown in FIG. 5 to be similar, can be individually shaped to include a plurality of portions if so desired. In operation, this particular embodiment is most advantageously utilized under conditions where it is desirable to either analyze a sample through serially connected analytical columns or to analyze two samples simultaneously.

While the description herein is specific to certain embodiments, it is to be considered exemplary only and is not deemed limiting. The present invention is considered limited only by the claims appended hereto and the reasonable interpretation thereof.

What is claimed is:

1. Apparatus useful for controlling the temperature of a chromatography column; said apparatus comprising:
    a first base member;
    first means, associated with said first base member,
        for receiving said column, said first means being adapted to substantially uniformly accept said column;

a second base member;

second means, associated with said second base member, for receiving said column, said second means being adapted to substantially uniformly accept said column, said first means and said second means being cooperatively formed such that the peripheral surface of said column can be substantially completely contacted thereby; and means for controlling the temperature of said first and said second means whereby said temperature of said column is controlled.

2. Apparatus as claimed in claim 1 wherein:

said first and said second means are detachably mounted to said first and said second base members.

3. Apparatus as claimed in claims 1 or 2 further comprising:

means for biasing said first and said second receiving means away from said first and said second base members respectively.

4. Apparatus as claimed in claim 3 wherein said biasing means includes coil springs within an aperture in each of said base members.

5. Apparatus as claimed in claims 1 or 2 further comprising:

means for retaining said first and said second receiving means adjacent said first and said second base members, respectively.

6. Apparatus as claimed in claim 1 wherein base members are hinged together such that upon closure thereof, said first and second means are adjacent.

7. Apparatus as claimed in claim 6 further including means for latching said members in a closed position.

8. Apparatus as claimed in claim 1 further including means affixed to each of said column receiving means for heating said means.

9. Apparatus as claimed in claim 8 wherein said heating means are independently encapsulated.

10. Apparatus as claimed in claim 1 further including:

means for sensing the temperature of said first and second column receiving means.

11. Apparatus as claimed in claim 1 wherein said first and second means each include multiple cavities.

12. Apparatus as claimed in claim 1 wherein said base members further comprise:

means for cooling said first and second means associated therewith.

13. Apparatus as claimed in claim 12 wherein said cooling means includes conduits within said members for conveying coolant fluid therethrough.

* * * * *